(12) United States Patent
Wozencroft

(10) Patent No.: US 10,905,563 B2
(45) Date of Patent: Feb. 2, 2021

(54) HOLDER FOR RESURFACING HEAD IMPLANT

(71) Applicant: Embody Orthopaedic Limited, London (GB)

(72) Inventor: Robert Wozencroft, Epsom (GB)

(73) Assignee: Embody Orthopaedic Limited, London (GB)

( * ) Notice: Subject to any disclaimer, the term of this patent is extended or adjusted under 35 U.S.C. 154(b) by 128 days.

(21) Appl. No.: 15/774,229

(22) PCT Filed: Nov. 7, 2016

(86) PCT No.: PCT/GB2016/053476
§ 371 (c)(1),
(2) Date: May 7, 2018

(87) PCT Pub. No.: WO2017/077342
PCT Pub. Date: May 11, 2017

(65) Prior Publication Data
US 2018/0325695 A1  Nov. 15, 2018

(30) Foreign Application Priority Data

Nov. 6, 2015  (GB) .................................. 1519629.8

(51) Int. Cl.
*A61F 2/46* (2006.01)
*A61F 2/30* (2006.01)
*A61F 2/36* (2006.01)

(52) U.S. Cl.
CPC .......... *A61F 2/4607* (2013.01); *A61F 2/3603* (2013.01); *A61F 2002/3071* (2013.01); *A61F 2002/3097* (2013.01); *A61F 2002/30507* (2013.01); *A61F 2002/30718* (2013.01); *A61F 2002/30968* (2013.01); *A61F 2002/30985* (2013.01);
(Continued)

(58) Field of Classification Search
CPC ................................. A61F 2/46; A61F 2/4607
See application file for complete search history.

(56) References Cited

U.S. PATENT DOCUMENTS 7,601,139 B2  10/2009 Woehr et al.
8,277,450 B2 * 10/2012 Dees, Jr. .............. A61B 17/154
279/42

(Continued)

FOREIGN PATENT DOCUMENTS

AU  2016348914 A1  5/2018
CA  3004406 A1  5/2017
(Continued)

OTHER PUBLICATIONS

International Searching Authority, International Search Report and Written Opinion for PCT/GB2016/053476 dated Feb. 3, 2017, 11 pages.

(Continued)

*Primary Examiner* — Christopher J Beccia
(74) *Attorney, Agent, or Firm* — Schwegman Lundberg & Woessner, P.A.

(57) ABSTRACT

A holder system for an implantable device, said holder system comprising a first component arranged to act as a clamp and a second component arranged to interact with the first component to prevent movement of said first component when clamped.

19 Claims, 4 Drawing Sheets

(52) U.S. Cl.
CPC ............ *A61F 2002/4628* (2013.01); *A61F 2002/4681* (2013.01); *A61F 2002/4687* (2013.01)

(56) References Cited

U.S. PATENT DOCUMENTS

| | | | |
|---|---|---|---|
| 9,078,710 B2* | 7/2015 | Thoren | A61B 17/7077 |
| 2003/0229357 A1* | 12/2003 | Dye | A61F 2/4637 |
| | | | 606/99 |
| 2005/0143749 A1* | 6/2005 | Zalenski | A61F 2/4611 |
| | | | 606/99 |
| 2005/0209597 A1 | 9/2005 | Long et al. | |
| 2008/0109085 A1 | 5/2008 | Tulkis et al. | |
| 2010/0318192 A1 | 12/2010 | Laffay et al. | |

FOREIGN PATENT DOCUMENTS

| | | |
|---|---|---|
| CN | 1921810 | 2/2007 |
| CN | 101257867 | 9/2008 |
| CN | 201461632 | 5/2010 |
| CN | 103501731 | 1/2014 |
| CN | 108366863 A | 8/2018 |
| DE | 16011397 | 5/1976 |
| EP | 1570816 | 9/2005 |
| EP | 3370656 A1 | 9/2018 |
| FR | 3008308 | 1/2015 |
| GB | 2406277 | 10/2003 |
| GB | 2406277 | 3/2005 |
| GB | 2522045 | 7/2015 |
| JP | 2007516789 | 6/2007 |
| WO | 9948436 | 9/1999 |
| WO | 2007028588 | 3/2007 |
| WO | 2009076293 | 6/2009 |
| WO | 2015044685 | 4/2015 |
| WO | WO-2017077342 A1 | 5/2017 |

OTHER PUBLICATIONS

"Chinese Application Serial No. 201680070620.X, Office Action dated Jun. 20, 2019", w English Translation, 16 pgs.

"European Application Serial No. 16794717.5, Response Filed Jan. 23, 2019 to Communication pursuant to Rules 161(2) and 162 EPC dated Jul. 13, 2018", 8 pgs.

"International Application Serial No. PCT/GB2016/053476, International Preliminary Report on Patentability dated May 17, 2018", 7 pgs.

"Chinese Application Serial No. 201680070620.X, Response filed Nov. 5, 2019 to Office Action dated Jun. 20, 2019", with English claims, 24 pages.

"Chinese Application Serial No. 201680070620.X, Office Action dated Apr. 9, 2020", with English translation, 20 pages.

"Chinese Application Serial No. 201680070620.X, Response filed Jun. 24, 2020 to Office Action dated Apr. 9, 2020", with English claims, 28 pages.

"Australian Application Serial No. 2016348914, First Examination Report dated Sep. 8, 2020", 4 pages.

"Japanese Application Serial No. 2018-543463, Notification of Reasons for Refusal dated Nov. 10, 2020", with English translation, 7 pages.

"Chinese Application Serial No. 201680070620.X, Office Action dated Nov. 10, 2020", with English translation, 22 pages.

* cited by examiner

HOLDER FOR RESURFACING HEAD IMPLANT

BACKGROUND

During a hip resurfacing operation, the head of the femur is shaped with rotary cutters and sometimes a flat saw cut, so that the internal profile of the resurfacing head implant fits the bone precisely. Resurfacing head implants can be either cemented or porous coated (cement free). In both cases the surgeon must forcibly impact the head onto the pre-prepared femoral bone. In the case of porous coated cement free implants, the bone is machined slightly oversized, so that initial stability of the implant on the bone is achieved via a small interference fit. Due to the relatively short cylindrical engagement between head internal diameter and bone, resurfacing heads usually include a central post which is inserted into a pre-drilled hole in the centre of the femoral head and guides the implant onto the bone. In the case of cemented resurfacing heads, this post also prevents low viscosity bone cement from squirting into the intramedullary bone canal via the central hole which is undesirable. Once implanted it is generally accepted that the central post is not required to carry load or to make any other functional contribution. Moreover there is increasing concern amongst orthopaedic surgeons and biomechanical engineers that there is an excessive amount of bone removal to accommodate a central post, particularly on smaller resurfacing head sizes which can weaken the bone. Furthermore, a large post can be loaded to some degree and contribute to stress shielding, leading to bone loss and possible implant failure. It is therefore desirable to reduce the size of, or completely remove the central post on a new generation of non-metal resurfacing implants, including those manufactured from zirconia toughened alumina ceramic (ZTA). However the issue of achieving initial head implant alignment on the remaining short stem and/or short cylindrical engagement between head internal bore and the prepared bone remains a concern. It has been observed that if the head implant starts to deviate off alignment during forcible impaction, it can become jammed at the wrong angle on the bone and become difficult to advance further or to remove to try again. Furthermore, the head implant bearing surface can be damaged during the forcible impaction process, introducing small scratches which can affect the performance of the bearing.

STATEMENT OF INVENTION

To overcome these issues, the present invention provides a holder for the resurfacing head implant which securely grips the implant and extends the length of the internal cylindrical portion to provide additional alignment during fitting onto the bone. Furthermore, the holder encapsulates the bearing surface, protecting it during forcible impaction.

DESCRIPTION AND ADVANTAGES

In the foregoing description, the system of the invention has been named as a holder system. However, as the system is used to hold an implantable device and guide the device onto the femoral head in the correct orientation, the system could as appropriately be classed as a guide system.

The present invention therefore provides a holder system for an implantable device, said holder system comprising a first component arranged to act as a clamp and a second component arranged to interact with the first component to prevent movement of said first component when clamped.

The invention also provides a holder system for an implantable device, said holder system comprising a first component arranged to act as a clamp, said component comprising an actuating portion and a jaw portion, said actuating portion and jaw portion arranged either side of a hinge region, wherein there is a cavity in the component defined by the walls of said component between the actuating portion and jaw portion and wherein the actuating portion is arranged such that access to the cavity is permitted via the actuating portion.

The first component generally comprises an actuating portion and a jaw portion. The actuating portion and jaw portion each comprises opposing arms arranged around a hinge, in a similar arrangement as a clothes peg.

The actuating portion and the jaw portion preferably each comprises at least two opposing arms, optionally 2, 3, 4, 5 or 6 opposing arms. The number of arms on the actuating portion and the jaw portion does not necessarily need to be the same.

In certain aspects of the invention, the arms of the actuating portion are substantially the same length. This is useful when there is a second component involved and where that second component is fixed to the actuating portion. In certain aspects of the invention, the arms of the jaw portion are substantially the same length.

The actuating portion will preferably provide a substantially cylindrical profile. It will be appreciated that the cylindrical profile does not need to be a fully formed cylinder. Instead, the walls of the actuating portion can have a number of gaps between the arms that make up the actuating portion. This is advantageous as it allows the compression and expansion of the opposing arms of the actuating portion in order to activate the jaw portion of the first component. By cylindrical it is meant that a substantially cylindrical profile is obtained if one were to imagine extension of the wall of the arms to a substantially cylindrical end point.

The holder system of the invention comprises a first component which defines an approximately cylindrical bore running through the component. The cylindrical bore can be extended by a cylindrical portion of the holder in the jaw portion, optionally approximately matching in size, to provide extended alignment with a bone (e.g. pre-machined femur bone) on which the holder is to be placed. This extension of the jaw portion of the first component therefore provides for a more accurate alignment of the implant onto the femur head, especially in scenarios where the implantable device may have a short or non-existent central post.

As discussed in more detail below, the actuating portion and jaw portion typically are arranged on either side of a hinge region such that when the actuating portion is compressed the jaw portion expands, and when the actuating portion is relaxed the jaw portion closes.

In the preferred use of the holder system, the first component must fit over an implantable device. In certain embodiments, this is a resurfacing hip implant which generally has a part-spherical surface. This fitting is partly achieved by expanding the jaw portion such that the arms of the jaw portion can fit over the implantable device and then be released when the implantable device has passed into a cavity within the first component. To this end, the holder is designed to define a cavity in the first component to accommodate the implantable device. Such a cavity is typically defined by the walls of the actuating portion and jaw portions. Preferably the cavity lies between the actuating portion and the jaw portion, optionally in the region of the hinge. The cavity generally has a larger profile than the rest of the first component, which reflects the ball-like structure of the implantable device. In some cases the cavity is a ballooned (expanded) profile, and in some circumstances this can be reasonably/approximately spherical.

In preferred aspects of the present invention, the jaw portion comprises at least one gripping portion, optionally wherein the gripping portion is profiled to increase frictional force with the intended item to be gripped. This gripping portion may define a ledge on the inner surface of the jaw portion. Such a ledge is typically at the distal (jaw-ward) end of the cavity, said ledge arranged to contact an edge of an implantable device so as to hold said implantable device within said cavity.

If the implantable device has any particular contour, then the ledge of the jaw portion is preferably contoured so as to accurately fit any contour present on the edge of the implantable device.

In certain arrangements, both the edge of the implantable device and the mating internal ledge of the jaw portion have a corresponding inward sloping angle which acts to increase the grip, security and rigidity of the overall assembly as the second component is tightened.

In order to present a secure clamping arrangement, in preferred scenarios of the holder system there is a second component present and wherein the second component prevents the first component from unclamping. Generally this is achieved by the second component interacting with the actuating portion.

Generally this interacting is achieved by the actuating portion and second component having complementary means for attaching to each other, such as a screw thread or a bayonet fitting.

Preferably the second component is arranged such that it interacts with both sides of the actuating portion in order to prevent the actuating portion from expansion or compression.

In preferred embodiments of the present invention the second component comprises a shaft and when the second component is fixed to the first component the shaft extends towards the cavity in the first component. When an implantable device is held in the cavity of the first component, the shaft of the second component is pressed upon said implantable device when said second component is fixed to said first component. This pressing from the shaft on the second component pushes the edge/rim of the implantable device against the ledge on the jaw portion of the first component, thereby forming a tight compression grip on the implantable device to prevent it from moving during use. Where the ledge on the jaw portion is contoured in a corresponding contour to that of the edge of the implantable device, it will be appreciated that there will only be relatively few ways in which the implantable device can align within the cavity—preferably only one way. In this manner, therefore, there is provided a way to securely and safely align the implantable device within the holder so that further installation of the implantable device is performed accurately.

During installation of the implantable device, typically the surgeon will be required to transmit a force to the implant. This is done preferably via a separate impaction shaft. In this regard, the second component further comprises a receptacle for an impaction shaft. The receptacle is positioned on the opposite side of the second component from the shaft. It may form or be part of the axis of the shaft. The receptacle may further comprises an indexing means so as to prevent rotation of the impaction shaft.

In some arrangements, the impaction shaft is assembled with the second component to position and impact the head implant into position, e.g. onto the preformed femur bone.

The first component may be made from a plastics material (e.g. nylon). Such a material is advantageous as it provides the hinge region with some resilience such that it flexes between an activated (on manipulation) and a relaxed state. In certain embodiments the first component is made from additive manufacturing, for example selective laser sintering (SLS). Likewise the second component can also be made from the same material and in the same manner as the first component.

The impaction shaft can be manufacture from any suitable robust material. In some aspects, the shaft is manufactured in metal (for example aluminium alloy or stainless steel).

The invention also provides for a computer-readable medium having computer-executable instructions adapted to cause a 3D printer to print a first component and/or second component of a holder system as defined herein.

The present invention also provides a method of holding an implantable device, said method comprising the use of a holder system comprising a first component arranged to act as a clamp, said component comprising an actuating portion and a jaw portion said actuating and jaw portions arranged either side of a hinge region, wherein there is a cavity in the component defined by the walls of said component between the actuating portion and jaw portion and wherein the actuating portion is arranged such that access to the cavity is permitted via the actuating portion, wherein said implantable device is inserted into said first component to lie within the cavity, said system further comprising a second component which is attached to said actuating portion of said first component and wherein said second component is arranged such that tightening of said second component onto said first component results in the implantable device within the cavity being securely gripped by the jaw portion.

As discussed above, optionally the implantable device and the gripping portions on the jaw portions have complementary contours such that the implantable device is specifically aligned within the cavity.

In use, the holder system is placed over a bone of interest (e.g. femur head) and pushed onto said bone such that said implantable device interacts with said bone. An impaction shaft is attached to said second component before or after said holder system is positioned over a bone. Thereafter, said second component is hit, optionally via an impaction shaft, so as to securely fix the implantable device in place.

Once the implantable device is appropriately positioned and fixed, the second component is removed from said first component and said first component is removed from said implantable device. Removal of said first component is aided by compressing the arms of said actuating portion, thereby resulting in the expansion of the arms of the jaw region such that the gripping portion is disassociated from the implantable device and said first component can thereafter be removed from the implantable device.

Supplemental Description & Advantages

The holder has a resilient hinge portion allowing it to be expanded and fitted over the head implant. The holder being approximately spherical in shape encapsulates the head implant to protect it during forcible impaction. The holder has an internal rim which fits exactly to the head implant rim. A separate locking collar is inserted and tightened preferably via a screw thread. The locking collar includes a short shaft with concave end which tightens onto the head implant. The head implant rim has an inward sloping angle, so that as the locking collar is tightened, it firmly grips the head implant between the rim and the top of the spherical bearing. Once assembled and tightened, the holder becomes very rigid and furthermore, because the holder is pulled tight against the head implant bearing diameter which is very accurately manufactured, the cylinder extension adopts the accuracy of the bearing resulting in an accurate and rigid cylinder extension to the implant internal diameter. The locking collar has an engagement feature to accept a separate metal shaft for manipulation and forcible impaction.

Once the head implant is finally fitted to the femoral bone, the shaft and locking collar are removed, so that the holder hinge portion is free to flex and the holder can be expanded over the head implant to remove it. During this removal process there is no force exerted on the head implant which could disrupt the fit on the femur bone. The holder and locking collar are manufactured from a plastic material (such as nylon) which will not damage the hard bearing surface. Preferably, the holder and locking collar are manufactured in plastic (for example nylon) by an additive manufacturing process, for example selective laser sintering (SLS). Preferably, the shaft for manipulation and impaction is manufactured from metal (such as aluminium alloy or stainless steel). Preferably, the shaft connection feature has a slight press fit into the locking collar so they remain fixed together once assembled. Alternatively, a reversible snap fit or a snap fit that requires releasing by the user may be used. Furthermore, the engaging feature will prevent rotation between the assembled holder and the shaft. In addition to the shaft, a patient specific head alignment guide may be employed to position the head onto the femur bone in accordance with a pre-operative bone scan and predetermined plan. As the opposite end of the shaft also has a rotation indexing feature, the alignment guide can direct the head implant into the planned rotational orientation on the femur bone. If further impaction of the head implant is required, the locking collar with shaft inserted can be employed separately, without the need to re-assemble the holder over the head implant.

A further feature of the invention is that the extended cylinder on the holder is shaped to match the asymmetric contoured shape of the head implant to provide a visual cue to the surgeon who must rotationally orientate the head implant appropriately on the bone. Furthermore, the holder has clear markings (for example 'superior' and 'inferior') to further guide the surgeon to the desired anatomical position.

INTRODUCTION TO DRAWINGS

An example of the invention will now be described by referencing to the accompanying drawings.

DESCRIPTION WITH REFERENCE TO DRAWINGS

Figure 1:
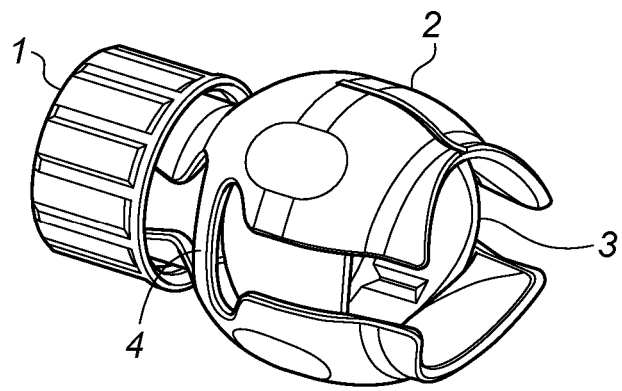
FIG. 1 is a complete holder, assembled on a resurfacing head implant.
Figure 2:
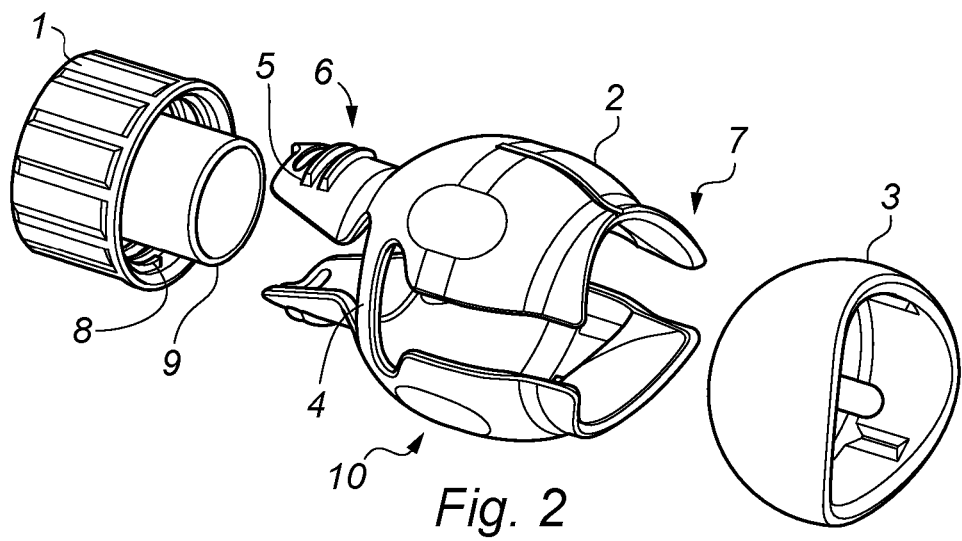
FIG. 2 is an exploded view of FIG. 1 showing the head implant, holder and locking collar.

In FIGS. 1 & 2 the three parts are identified as resurfacing head implant (3), holder (2) and locking collar (1). Also visible are thinned resilient sections (4) of the holder (2) which act approximately as a hinge as will be described below.

Figure 3:
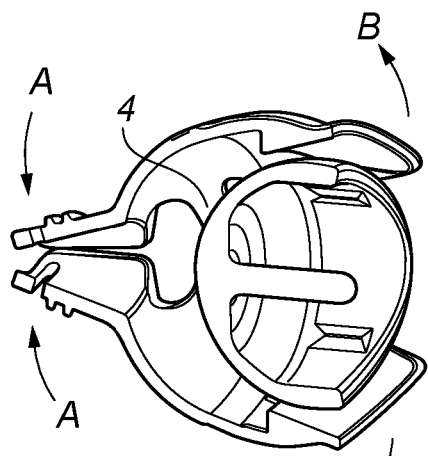
FIG. 3 is a cross sectioned view of the holder of FIG. 1 being assembled over the head implant.
Figure 4:
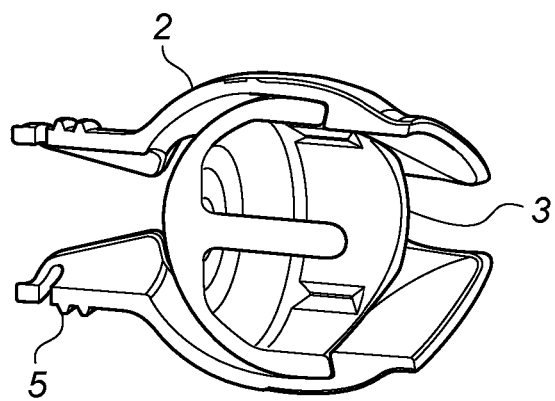
FIG. 4 is a cross sectioned view of the holder of FIG. 1 assembled on the head implant.
Figure 5:
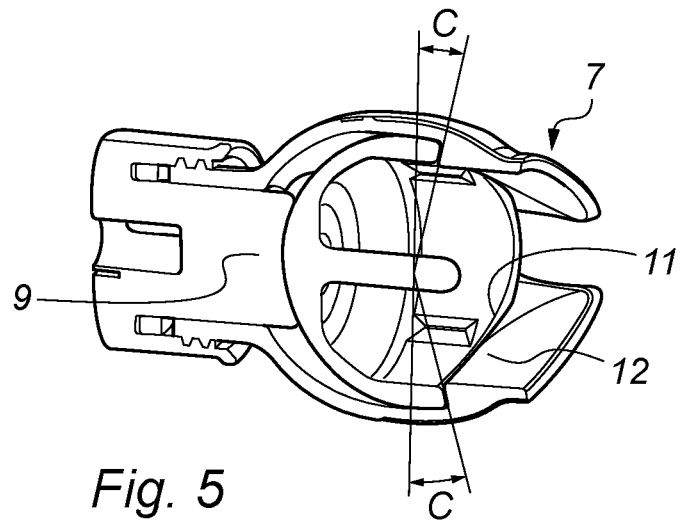
FIG. 5 is a cross sectioned view of the holder and locking collar of FIG. 1 assembled on the head implant.
Figure 6:
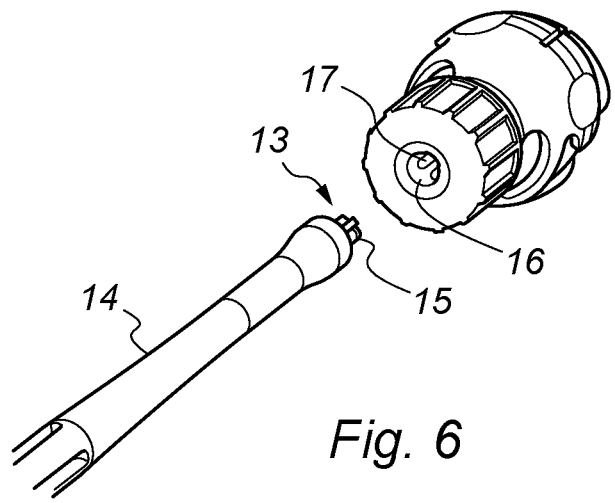
FIG. 6 is the complete holder of FIG. 1 with impaction shaft being inserted. It shows the engaging and anti-rotation features between locking collar and impaction shaft.
Figure 7:
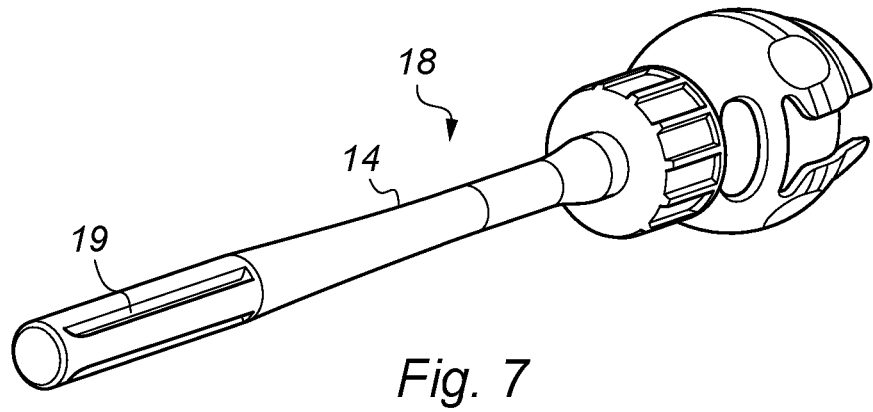
FIG. 7 is the complete holder of FIG. 1 with head implant and impaction shaft.
Figure 8:
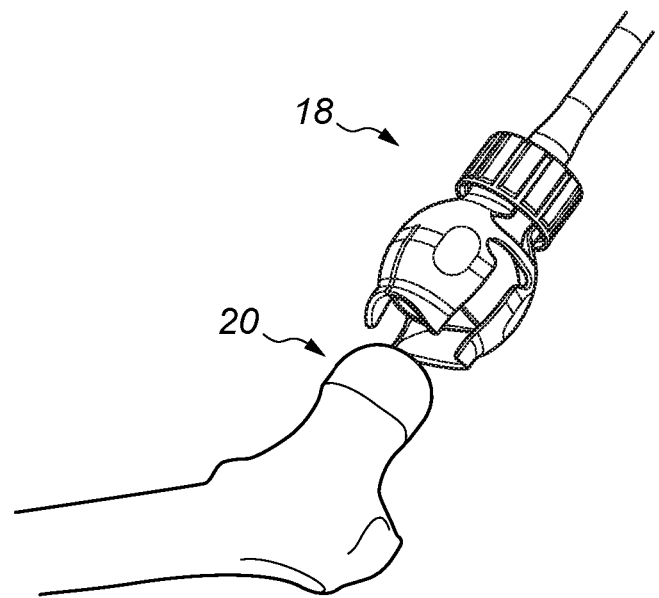
FIG. 8 is the complete holder of FIG. 7 with head implant and impaction shaft about to be impacted onto the pre-prepared femur bone.
Figure 9:
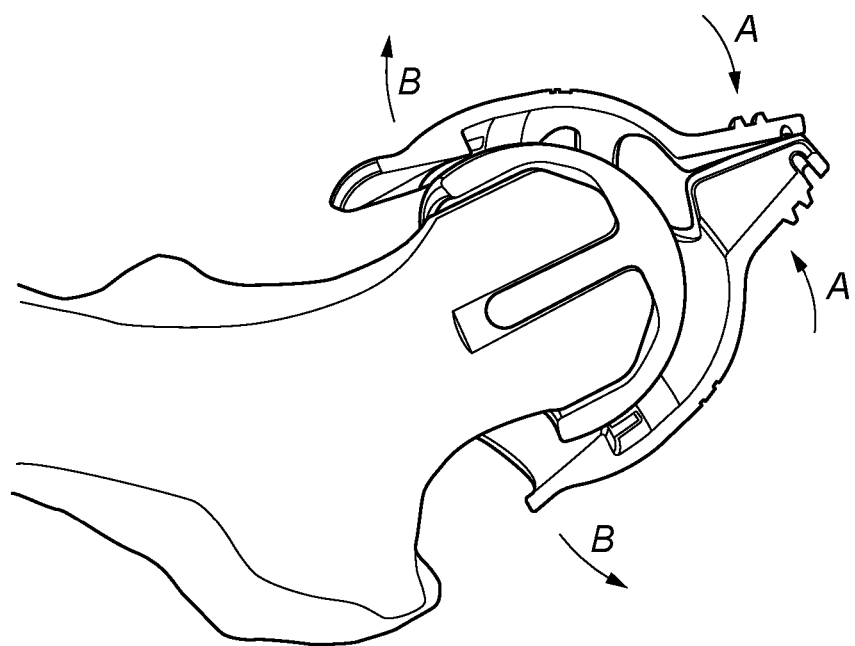
FIG. 9 shows the holder of FIG. 8 being removed over the implant which is fully impacted onto the femur bone.
Figure 10:
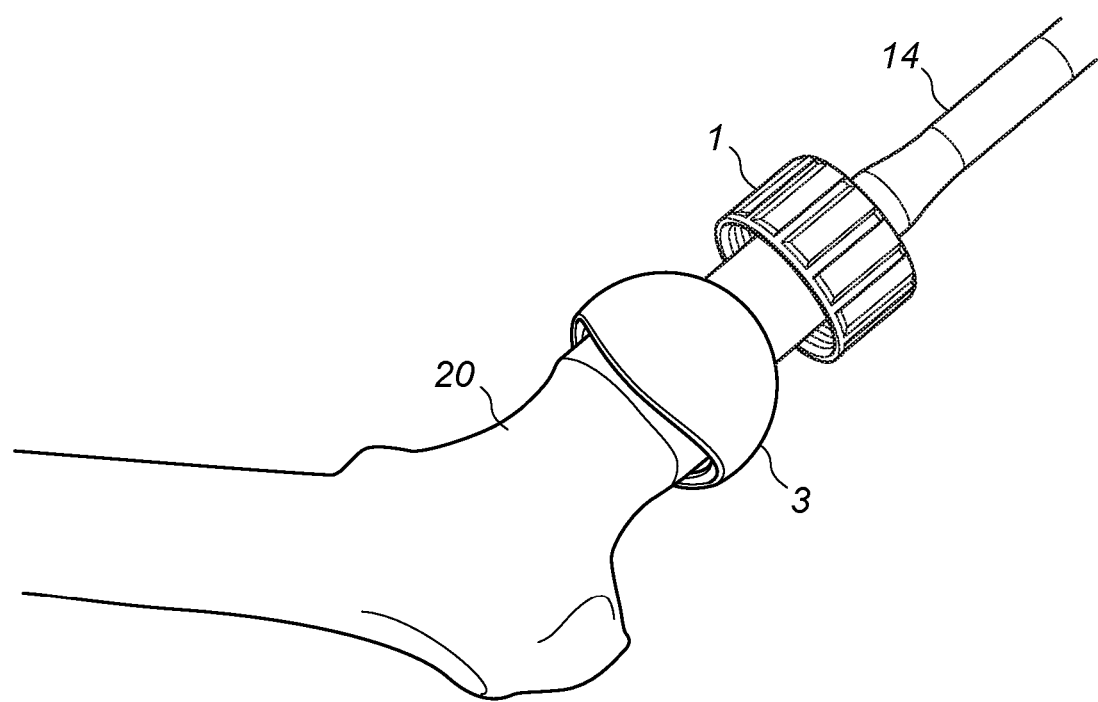
FIG. 10 is a locking collar and impaction shaft being employed without a holder to further impact a head implant.

In use the locking collar (1) is unscrewed via engaging male and female screw thread (5 & 8 respectively) and separated. It is then possible to compress the threaded portion (6) of the holder (2) with a manual pinch grip, for example between thumb and forefinger (not shown) in the direction of arrows (A) (see FIG. 3). As the threaded section is compressed, the largely spherical portion (10) at the other side of the resilient hinge expands in the direction of arrows (B) as shown in FIG. 3. The partial male thread features (5) also act as a grip for the fingers and thumb. When fully expanded, the resurfacing head implant (3) passes easily within the largely spherical portion (10) to assemble it and, as the pinch grip is relaxed, the holder closes around the head implant to encapsulate it as shown in FIG. 4. The locking collar (1) is then assembled via the engaging male and female screw thread (5 & 8 respectively) and shaft (9) is tightened onto the top of the head implant (3) as shown in FIG. 5. The contoured rim (11) of the head implant fits an internal ledge (12) of the holder (2) as shown in FIGS. 4 & 5. The grip of the holder onto the head implant is enhanced as the shaft (9) of the locking collar is tightened against the head implant because there is a corresponding inward sloping angle (angle C) on the head implant rim and holder internal ledge (see FIG. 5). Therefore the more it is tightened, the more securely the head implant is gripped and the more rigid the overall assembly becomes. It can also be seen in FIG. 5 that the cylindrical portion of the head implant bore is extended to approximately twice its original length by the cylindrical portion of the holder (7). A shaft (14) is inserted into the holder assembly via a spigot (13) which fits into the bore of the locking collar (16). A small interference fit ensures that they remain fixed together once assembled. A rotational alignment feature (17) corresponds with a mating rotational orientation feature on the shaft (15) to prevent rotation between the shaft and holder assembly (18) as shown in FIG. 6. FIG. 7 shows the opposite end rotational indexing feature (19) which mates with an optional head alignment guide (not shown) to optionally rotationally orientate the head in accordance with a pre-operative plan. The shaft is then used to position and impact the head implant onto the pre-machined femur bone (20) as shown in FIG. 8. The extended cylindrical portion (7) of the holder ensures that the head implant is correctly aligned with the bone prior to and during forcible impaction. The inward sloping angle (C) on the head implant rim and holder ledge also acts to ensure full contact between the holder bore and implant bearing surface which is very accurately manufactured. Therefore the cylinder extension of the holder takes on accuracy and stiffness from the head implant, and the fit on the machined bone is therefore well controlled. When fully impacted, the locking collar (1) and shaft (14) are removed and It is then possible to remove the holder by compressing the threaded section of the holder which expands the spherical portion (as described previously) allowing removal of the holder over the implanted head implant as shown in FIG. 9. When fully expanded, the holder passes easily over the head implant without disrupting the fixation with the femur bone. In rare circumstances such as a very short neck of femur, the cylinder extension may impinge with bone further down the neck, preventing further advancement of the head implant. In such circumstances the holder (2) is removed (as described above) and the locking collar (1) with shaft (14) still attached is used independently to fully impact the head implant as shown in FIG. 10.

The invention claimed is:

1. A holder system for an implantable device, said holder system comprising:
    a first component, said first component comprising:
    an actuating portion;
    a jaw portion;
    a hinge region, wherein said actuating portion and jaw portion are arranged on either side of the hinge region, such that when the actuating portion is compressed the jaw portion expands, and when the actuating portion is relaxed the jaw portion closes; and
    a cavity defined by walls of said first component between the actuating portion and jaw portion, wherein the actuating portion is arranged such that access to the cavity is permitted via the actuating portion.

2. The holder system of claim 1, wherein the actuating portion and jaw portion each comprises opposing arms.

3. The holder system of claim 1, wherein the actuating portion comprises at least two opposing arms of substantially the same length.

4. The holder system of claim 1, wherein the jaw portion comprises at least two opposing arms.

5. The holder system according to claim 4, wherein either:
    (i) the arms of the jaw portion are defined preoperatively to exactly fit to a specific patient's bone and thereby orientate the holder according to a preoperative plan; or
    (ii) the arms of the jaw portion are defined to fit approximately to a certain size range of femoral necks without patient specific adaptations; or
    (iii) the arms of the jaw portion are substantially the same length.

6. The holder system of claim 1, wherein the first component defines an approximately cylindrical bore running through the actuating portion, wherein said cylindrical bore is extended by a cylindrical portion at the distal end of the jaw portion to provide extended alignment with a bone on which the holder is to be placed.

7. The holder system of claim 1, wherein;
    (i) the jaw portion comprises at least one gripping portion, optionally wherein the gripping portion is profiled to increase frictional force with the intended item to be gripped; and/or
    (ii) the actuating portion of the first component defines a substantially cylindrical profile.

8. The holder system of claim 1, wherein the cavity has a ballooned profile, optionally wherein the ballooned profile is approximately spherical.

9. The holder system of claim 1, wherein the jaw portion comprises an internal ledge at the jaw-ward end of the cavity, said ledge arranged to contact an edge of an implantable device so as to hold said implantable device within said cavity, and wherein said ledge is contoured so as to accurately fit a contour present on the edge of the implantable device.

10. The holder system of claim 9, further comprising a second component for coupling to the actuating portion of the first component, wherein both the edge of the implantable device and the mating internal ledge of the jaw portion have a corresponding inward sloping angle which acts to increase the grip, security and rigidity of the overall assembly as the second component is tightened against the actuating portion of the first component.

11. A holder system for an implantable device, said holder system comprising:
    a first component, said first component comprising:
    an actuating portion;
    a jaw portion;
    a hinge region, wherein said actuating portion and jaw portion are arranged on either side of the hinge region; and
    a cavity defined by walls of said first component between the actuating portion and jaw portion, wherein the actuating portion is arranged such that access to the cavity is permitted via the actuating portion; and
    a second component for coupling to the actuating portion of the first component, wherein when the second component is coupled to the first component the second component prevents the first component from unclamping an implantable device arranged in the cavity of the first component.

12. The holder system of claim 11, wherein said second component is a locking collar which is inserted and tightened onto the first component via;
    (i) a screw thread which blocks expansion and increases the clamping force of the jaw portion; or
    (ii) bayonet fitting or press fit which blocks expansion and increases the clamping force of the jaw portion.

13. The holder system of claim 11, wherein the second component is arranged such that it interacts with the actuating portion in order to prevent the actuating portion from expansion or compression.

14. The holder system of claim 11, wherein the second component comprises a shaft and wherein when the second component is fixed to the first component the shaft extends towards the cavity in the first component, and wherein when an implantable device is held in the cavity of the first component the shaft of the second component is pressed upon said implantable device when said second component is fixed to said first component.

15. A holder system of claim 11, wherein the first and/or second components are manufactured in plastic by an additive manufacturing process.

16. A method, comprising;
    inserting an implantable device into a cavity of a first component of a holder system, wherein said first component comprises:
    an actuating portion;
    a jaw portion;
    a hinge portion, wherein said actuating and jaw portions arranged either side of the hinge region; and
    a cavity defined by walls of said first component between the actuating portion and jaw portion, wherein access to the cavity is permitted via the actuating portion and the jaw portion; and
    attaching a second component of the holder system to said actuating portion of said first component, wherein said first and second components are configured such that tightening of said second component onto said first component results in the implantable device within the cavity being securely gripped by the jaw portion.

17. The method of claim 16, wherein said implantable device and gripping portions of the jaw portion have complementary contours such that the implantable device is specifically aligned within the cavity.

18. The method of claim 16, further comprising:
removing said second component from said first component;
subsequently compressing arms of the actuating portion of the first component, thereby resulting in the expansion of the jaw region such that a gripping portion of the jaw region is disassociated from the implantable device; and
removing said first component from said implantable device.

19. The holder system of claim 1, wherein the hinge region comprises thinned resilient sections of the first component.

* * * * *